US00PP15124P2

(12) United States Plant Patent
Brown

(10) Patent No.: US PP15,124 P2
(45) Date of Patent: Aug. 31, 2004

(54) HELENIUM PLANT NAMED 'HELBRO'

(50) Latin Name: *Helenium hybrida*
Varietal Denomination: Helbro

(75) Inventor: Bob Brown, Fladbury (GB)

(73) Assignee: Blooms of Bressingham, Ltd., Bressingham (GB)

( * ) Notice: Subject to any disclaimer, the term of this patent is extended or adjusted under 35 U.S.C. 154(b) by 0 days.

(21) Appl. No.: 10/602,091

(22) Filed: Jun. 23, 2003

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—C. A. Whealy

(57) ABSTRACT

A new and distinct cultivar of Helenium plant named 'Helbro', characterized by its upright and somewhat outwardly spreading plant habit; freely basal branching growth habit; freely flowering habit; large upright-facing inflorescences with yellow and red bi-colored ray florets; and strong and erect peduncles that tolerate wind and rain.

1 Drawing Sheet

Botanical classification/cultivar designation: Helenium hybrida cultivar Helbro.

BACKGROUND OF THE INVENTION

The present Invention relates to a new and distinct cultivar of Helenium plant, botanically known as Helenium hybrida, and hereinafter referred to by the name 'Helbro'.

The new Helenium was discovered as a chance seedling of two unidentified selections of Helenium hybrida, not patented. The new Helenium was discovered and selected by the Inventor in 1996 as a single flowering plant in a controlled environment in Worcester, United Kingdom.

Asexual reproduction of the new Helenium by cuttings was first conducted in Worcester, United Kingdom in June, 1996. Since then, asexual reproduction by divisions has shown that the unique features of this new Helenium are stable and reproduced true to type in successive generations.

SUMMARY OF THE INVENTION

The cultivar Helbro has not been observed under all possible environmental conditions. The phenotype may vary somewhat with variations in environment such as temperature and light intensity without, however, any variance in genotype.

The following traits have been repeatedly observed and are determined to be the unique characteristics of 'Helbro'. These characteristics in combination distinguish 'Helbro' as a new and distinct Helenium:

1. Upright and somewhat outwardly spreading plant habit.
2. Freely basal branching growth habit.
3. Freely flowering habit.
4. Large upright-facing inflorescences with yellow and red bi-colored ray florets.
5. Strong and erect peduncles that tolerate wind and rain.

Plants of the new Helenium differ primarily from plants of the parent selections in ray and disc floret coloration.

Plants of the new Helenium can be compared to plants of the Helenium cultivar Coppelia, not patented. In side-by-side comparisons conducted in Worcester, United Kingdom, plants of the new Helenium differed from plants of the cultivar Coppelia in the following characteristics:

1. Plants of the new Helenium were larger than plants of the cultivar Coppelia.
2. Plants of the new Helenium had larger leaves and inflorescences than plants of the cultivar Coppelia.
3. Plants of the new Helenium were more freely flowering than plants of the cultivar Coppelia.
4. Plants of the new Helenium and the cultivar Coppelia differed in ray floret coloration as plants of the cultivar Coppelia had red-colored ray florets.
5. Plants of the new Helenium had stronger, longer and thicker peduncles than plants of the cultivar Coppelia.

BRIEF DESCRIPTION OF THE PHOTOGRAPH

The accompanying colored photograph illustrates the overall appearance of the new Helenium showing the colors as true as it is reasonably possible to obtain in colored reproductions of this type. Colors in the photograph may differ from the color values cited in the detailed botanical description which accurately describe the colors of the new Helenium. The photograph comprises a close-up view of typical inflorescences and leaves of typical flowering plants of 'Helbro' grown in an outdoor nursery.

DETAILED BOTANICAL DESCRIPTION

The aforementioned photograph and following observations and measurements describe plants grown in Bressingham, Diss, Norfolk, United Kingdom, under outdoor field conditions which closely approximate commercial production conditions. During the production of the plants, day temperatures ranged from 5 to 28° C. and night temperatures ranged from −8 to 15° C. Plants used for the photograph and description were grown for two growing seasons in 5-liter containers.

In the following description, color references are made to The Royal Horticultural Society Colour Chart, 1995 Edition, except where general terms of ordinary dictionary significance are used.

Botanical classification: Helenium hybrida cultivar Helbro.
Parentage:

*Female, or seed, parent.*—Unidentified selection of Helenium hybrida, not patented.

*Male, or pollen, parent.*—Unidentified selection of Helenium hybrida, not patented.

Propagation:

*Type.*—By cuttings.

*Time to initiate roots.*—About 10 days at 20° C.

*Time to produce a rooted cutting.*—About 20 days at 20° C.

*Root description.*—Fibrous, thin, freely branching, and grayed white to orangish brown in color.

Plant description:

*Appearance.*—Perennial herbaceous container and garden plant. Upright and somewhat outwardly spreading plant habit. Freely basal branching with clumps of basal leaves with inflorescences on erect and strong peduncles; dense and full plants.

*Plant height.*—About 100 cm.

*Plant width or area of spread.*—About 70 cm.

*Foliage description.*—Arrangement: Basal; simple; sessile. Length: About 10 cm. Width: About 3.5 cm. Shape: Obovate. Apex: Obtuse. Base: Cuneate. Margin: Entire. Venation pattern: Pinnate. Texture, upper and lower surfaces: Pubescent; slightly rough. Color: Developing foliage, upper surface: 146A. Developing foliage, lower surface: 146B. Fully expanded foliage, upper surface: 146C. Fully expanded foliage, lower surface: 146D. Venation, upper and lower surfaces: 146D.

Inflorescence description:

*Appearance.*—Single inflorescences held above the foliage on strong erect peduncles. Composite inflorescence form, radially symmetrical; elongated oblong-shaped ray florets; disc florets massed at the center; ray and disc florets develop acropetally on a capitulum. Inflorescences persistent. Inflorescences face mostly upright. Inflorescences flat, reflexing with development.

*Flowering response.*—Plants flower continuous and freely from July through the end of August in Norfolk, United Kingdom.

*Postproduction longevity.*—Inflorescences maintain good color and substance for about 52 days on the plant when grown in an outdoor environment.

*Quantity of inflorescences.*—Freely flowering; about 150 inflorescences per plant develop during the flowering season.

*Fragrance.*—None detected.

*Inflorescence bud* (*at stage of showing color*).—Length: About 3 cm. Diameter: About 3 cm. Shape: Orbicular. Color: 146D.

*Inflorescence size.*—Diameter: About 6 cm. Depth (height): About 3 cm. Disc diameter: About 3 cm. Receptacle height: About 1 cm. Receptacle diameter: About 2 cm.

*Ray florets.*—Length: About 3 cm. Width: About 2.5 cm. Shape: Oblong. Apex: Emarginate. Base: Fused into a short corolla tube. Margin: Entire, undulate. Texture, upper and lower surfaces: Smooth, glabrous. Orientation: Initially upright then perpendicular to the peduncle eventually reflexing. Number of ray florets per inflorescence: About 15 in one or two whorls. Color: When opening, upper surface: 44B flushed with 17B. When opening, lower surface: 44C flushed with 17C. Fully opened, upper surface: 44B flushed with 17B; color becoming closer to 167B with development. Fully opened, lower surface: 44D flushed with 17D.

*Disc florets.*—Shape: Tubular, elongated. Apex: Five-pointed; acute. Length: About 1 cm. Width: About 1 mm. Number of disc florets per inflorescence: About 150. Color, immature: 166A. Color, mature: Apex and mid-section: 166A. Base: 17B.

*Phyllaries.*—Length: About 9 mm. Diameter: About 2 mm. Shape: Linear. Apex: Acute. Base: Cuneate. Margin: Entire. Texture: Slightly rough; moderately pubescent. Number per inflorescence: About 55. Color, upper surface: 146C becoming flushed with 181B. Color, lower surface: 146D becoming flushed with 181B.

*Peduncles.*—Length: About 8 to 12 cm. Diameter: About 2 mm. Angle: Mostly erect to 20° from vertical. Strength: Strong. Texture: Longitudinally ribbed. Color: 146C becoming flushed with 181B.

*Reproductive organs.*—Androecium: Present on disc florets only. Stamen number: One per floret. Anther shape: Rounded. Anther length: About 1 mm. Anther color: 164A. Pollen amount: Scarce. Pollen color: 12B. Gynoecium: Present on both ray and disc florets. Pistil number: One per floret. Pistil length: About 1 mm. Stigma shape: Rounded. Stigma color: 17B. Style length: About 2 mm. Style color: 193D. Ovary color: 193D.

*Seed.*—Length: About 1 mm. Diameter: About 0.25 mm. Color: 166B.

Disease/pest resistance: Resistance to pathogens and pests common to Heleniums has not been observed on plants grown under outdoor conditions.

Weather tolerance: Plants of the new Helenium have been observed to tolerate rain, wind and temperatures from about −8 to 30° C.

It is claimed:

1. A new and distinct cultivar of Helenium plant named 'Helbro', as illustrated and described.

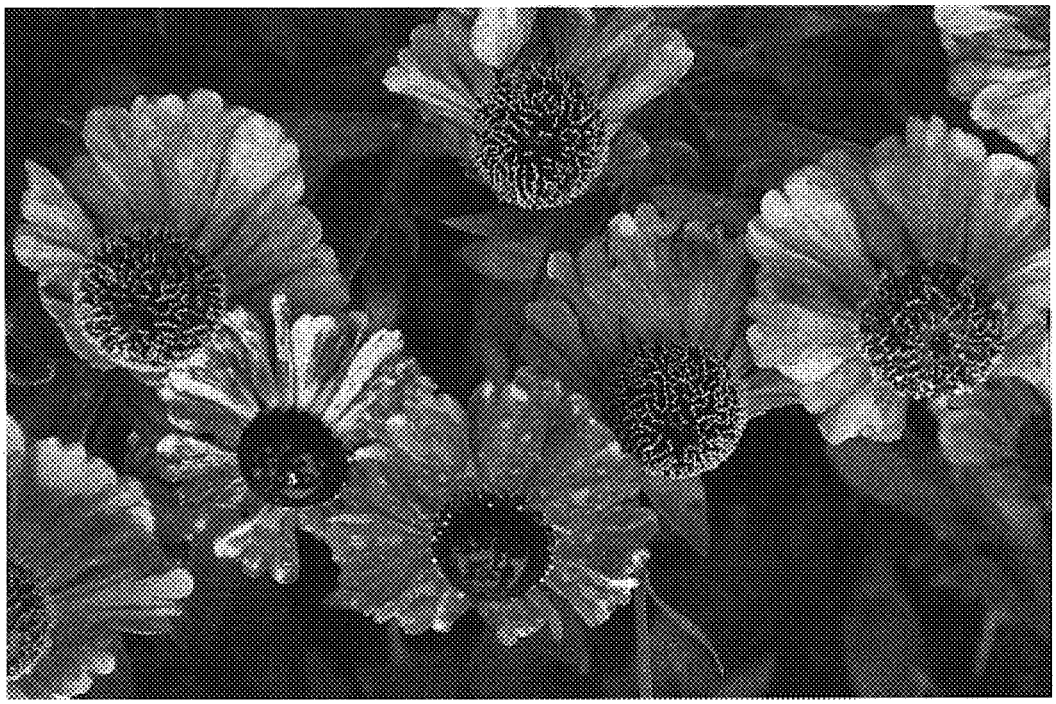

* * * * *